United States Patent
King et al.

(10) Patent No.: US 12,398,083 B2
(45) Date of Patent: Aug. 26, 2025

(54) MOBILE GAS PROCESSING PLANT

(71) Applicant: TYPHON TECHNOLOGY SOLUTIONS (U.S.), LLC, The Woodlands, TX (US)

(72) Inventors: Toby King, The Woodlands, TX (US); Jeffrey Morris, The Woodlands, TX (US)

(73) Assignee: Typhon Technology Solutions (U.S.), LLC, The Woodlands, TX (US)

( * ) Notice: Subject to any disclaimer, the term of this patent is extended or adjusted under 35 U.S.C. 154(b) by 743 days.

(21) Appl. No.: 17/579,969

(22) Filed: Jan. 20, 2022

(65) Prior Publication Data

US 2023/0227383 A1     Jul. 20, 2023

(51) Int. Cl.
*B01D 46/62*  (2022.01)
*B01D 46/00*  (2022.01)
(Continued)

(52) U.S. Cl.
CPC .......... *C07C 7/005* (2013.01); *B01D 46/0036* (2013.01); *B01D 46/62* (2022.01);
(Continued)

(58) Field of Classification Search
CPC ........ B01D 46/00; B01D 46/62; B01D 53/18; B01D 53/26; C07C 7/00; C07C 7/11;
(Continued)

(56) References Cited

U.S. PATENT DOCUMENTS

| | | | |
|---|---|---|---|
| 6,485,292 B1 * | 11/2002 | Rhodes | F23G 7/085 95/166 |
| 10,005,976 B2 | 6/2018 | Murray et al. | |

(Continued)

FOREIGN PATENT DOCUMENTS

| | | |
|---|---|---|
| CN | 109224783 A1 | 1/2019 |
| CN | 111735041 A | 10/2020 |

(Continued)

OTHER PUBLICATIONS

PCT Invitation to Pay Additional Fees, PCT Application No. PCT/US2023/10902, Apr. 4, 2023, 3 pages.
(Continued)

*Primary Examiner* — Sharon Pregler
(74) *Attorney, Agent, or Firm* — Fenwick & West LLP

(57) ABSTRACT

A mobile gas processing plant includes an inlet and an outlet, first and second Joule-Thompson (JT) valve units, an inlet scrubber, a dehydration unit including a contact tower, inlet and outlet filter separators, a vertical separator, and a dual pass line heater including first and second heating coils. The mobile gas processing plant is a mobile unit that is permanently mounted on at least one transport. The dehydration unit includes a contact tower that is permanently mounted on the at least one transport such that the contact tower is rotated up to be in an upright position relative to a base frame of the transport in an operational mode, and the contact tower is rotated down to be in a prostrated position relative to the base frame in a transportation mode. Each of the first and second JT valve units includes a first JT valve and a second JT valve. In the operational mode, and for each of the first and second JT valve units, a hydrocarbon gas stream flows through one of the first and second JT valves operating as a primary valve, and does not flow through the other of the first and second JT valves operating as a backup valve.

19 Claims, 10 Drawing Sheets

(51) Int. Cl.
*B01D 53/18* (2006.01)
*B01D 53/26* (2006.01)
*C07C 7/00* (2006.01)
*C07C 7/11* (2006.01)
*C10G 53/08* (2006.01)

(52) U.S. Cl.
CPC ........... *B01D 53/18* (2013.01); *B01D 53/261* (2013.01); *C07C 7/11* (2013.01); *C10G 53/08* (2013.01)

(58) Field of Classification Search
CPC .. C10G 53/08; C10G 5/06; C10L 3/10; C10L 3/101; C10L 3/106; F25J 3/0209; F25J 3/0233; F25J 3/0238; F25J 3/0242; F25J 3/08

See application file for complete search history.

(56) References Cited

U.S. PATENT DOCUMENTS

| | | | |
|---|---|---|---|
| 10,633,960 B2 | 4/2020 | Graney et al. | |
| 2013/0036671 A1* | 2/2013 | Saccheri | C10L 1/04 48/62 R |
| 2014/0174122 A1 | 6/2014 | Cooper et al. | |
| 2014/0231412 A1* | 8/2014 | Fowler | H05B 3/16 219/552 |
| 2014/0366577 A1* | 12/2014 | Zubrin | C10L 3/10 62/619 |
| 2016/0024409 A1 | 1/2016 | Murray et al. | |
| 2016/0097011 A1 | 4/2016 | Murray et al. | |
| 2017/0247482 A1 | 8/2017 | Moorhouse et al. | |
| 2019/0353303 A1 | 11/2019 | Morris et al. | |
| 2021/0301634 A1 | 9/2021 | Moneyhun et al. | |

FOREIGN PATENT DOCUMENTS

| | | |
|---|---|---|
| KR | 102022864 B1 | 9/2019 |
| WO | WO 2004/070297 A1 | 8/2004 |
| WO | 2013022501 A1 | 2/2013 |

OTHER PUBLICATIONS

PCT International Search Report and Written Opinion, PCT Application No. PCT/US2023/10902, Jul. 20, 2023, 14 pages.
English EPO and Google English Translation of CN109224783, published on Jan. 18, 2019, 10 pages.
Pro-Gas Services, LLC, "Natural Gas Production Facilities", https://www.progasllc.com/services/production-facilities/, 2021, 9 pages.
Transtex, LLC "JT Skids", HTTPS://Transtextreating.com/contact-us/, 2021, 4 pages.

* cited by examiner

MOBILE GAS PROCESSING PLANT

BACKGROUND

Hydraulic fracturing has been commonly used by the oil and gas industry to stimulate production of hydrocarbon producing wells, such as oil and/or gas wells. Hydraulic fracturing, sometimes called "fracing" or "fracking" is the process of injecting fracturing fluid, which is typically a mixture of water, proppants (e.g., fracturing sand, ceramics and resin coated materials), and chemicals, into the wellbore to fracture subsurface geological formations and release hydrocarbon reserves. The fracturing fluid is pumped into a wellbore at a pressure to cause fissures within the underground geological formations. Once inside the wellbore, the pressurized fracturing fluid flows into the subsurface geological formation to fracture the underground formation. The fracturing fluid may include water, various chemical additives, and proppants that promote the extraction of hydrocarbon reserves, such as oil and/or gas. Proppants, such as fracturing sand, prevent the fissures and fractures created in the underground formation from closing, and allow the formation to remain open so that the hydrocarbon reserves are able to flow to the surface.

Implementing fracturing operations at well sites typically requires extensive investment in equipment, labor, and fuel. For instance, a typical fracturing operation uses a variety of fracturing equipment, numerous personnel to operate and maintain the fracturing equipment, relatively large amounts of fuel to power the fracturing operations, and relatively large volumes of fracturing fluids. As such, planning for fracturing operations is often complex and encompasses a variety of logistical challenges that include minimizing the on-site area or "footprint" of the fracturing operations, providing adequate power and/or fuel to continuously power the fracturing operations, increasing the efficiency of the hydraulic fracturing equipment, and reducing any environmental impact resulting from fracturing operations. Thus, numerous innovations and improvements of existing fracturing technology are needed to address the variety of complex and logistical challenges faced in today's fracturing operations.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one embodiment, a mobile gas processing transport comprises: a base frame; an inlet and an outlet; a first Joule-Thompson (JT) valve unit, and a second JT valve unit; an inlet scrubber; a dehydration unit including a contact tower; an inlet filter separator and an outlet filter separator; and a vertical separator; wherein the first and second JT valve units, the inlet scrubber, the dehydration unit, the inlet and outlet filter separators, and the vertical separator, are mounted on the base frame of the mobile gas processing transport.

In another embodiment, a method for processing a raw or partially processed hydrocarbon gas mixture comprises: receiving, at a mobile gas processing plant, the raw or partially processed hydrocarbon gas mixture; flowing the received hydrocarbon gas mixture through a first JT valve unit to convert a portion of the hydrocarbon gas mixture into a liquid-phase; removing the liquid-phase of the hydrocarbon gas mixture by flowing the hydrocarbon gas mixture through an inlet scrubber to output a first hydrocarbon gas mixture; filtering the first hydrocarbon gas mixture by flowing the first separated hydrocarbon gas mixture through an inlet filter separator including a filter bank having at least one air filter to generate a second hydrocarbon gas mixture; heating the second hydrocarbon gas mixture by flowing the second hydrocarbon gas mixture into a contact tower of a dehydration unit to generate a third hydrocarbon gas mixture; flowing the third hydrocarbon gas mixture through a second JT valve unit to convert a portion of the third hydrocarbon gas mixture into a liquid-phase; removing the liquid-phase of the third hydrocarbon gas mixture by flowing the third hydrocarbon gas mixture through a vertical separator to output a fourth hydrocarbon gas; filtering the fourth hydrocarbon gas by flowing the fourth hydrocarbon gas through an outlet filter separator including a filter bank having at least one air filter to generate a fifth hydrocarbon gas; and outputting, from the mobile gas processing plant, the fifth hydrocarbon gas as purified, sales quality hydrocarbon gas for use as fuel by a mobile electric power generation system.

In yet another embodiment, a method for processing a raw or partially processed hydrocarbon gas mixture comprises: receiving, at a mobile gas processing plant, the raw or partially processed hydrocarbon gas mixture; flowing the received hydrocarbon gas mixture through a first JT valve unit to convert a portion of the hydrocarbon gas mixture into a liquid-phase; removing the liquid-phase of the hydrocarbon gas mixture by flowing the hydrocarbon gas mixture through an inlet scrubber to output a first hydrocarbon gas mixture; filtering the first hydrocarbon gas mixture by flowing the first separated hydrocarbon gas mixture through an inlet filter separator including a filter bank having at least one air filter to generate a second hydrocarbon gas mixture; heating the second hydrocarbon gas mixture by flowing the second hydrocarbon gas mixture into a first heating coil of a dual pass line heater to generate a third hydrocarbon gas mixture; flowing the third hydrocarbon gas mixture through a second JT valve unit to convert a portion of the third hydrocarbon gas mixture into a liquid-phase; removing the liquid-phase of the third hydrocarbon gas mixture by flowing the third hydrocarbon gas mixture through a vertical separator to output a fourth hydrocarbon gas; filtering the fourth hydrocarbon gas by flowing the fourth hydrocarbon gas through an outlet filter separator including a filter bank having at least one air filter to generate a fifth hydrocarbon gas; heating the fifth hydrocarbon gas by flowing the fifth hydrocarbon gas into a second heating coil of the dual pass line heater to generate a sixth hydrocarbon gas; and outputting, from the mobile gas processing plant, the sixth hydrocarbon gas as purified, sales quality hydrocarbon gas for use as fuel by a mobile electric power generation system.

In yet another embodiment, a mobile gas processing plant comprises: an inlet and an outlet; first and second Joule-Thompson (JT) valve units; an inlet scrubber; a dehydration unit including a contact tower; inlet and outlet filter separators; a vertical separator; and a dual pass line heater including first and second heating coils; wherein the mobile gas processing plant is a mobile unit that is permanently mounted on at least one transport; and wherein the dehydration unit includes a contact tower, and wherein the contact tower is permanently mounted on the at least one transport such that the contact tower is rotated up to be in an upright position relative to a base frame of the transport in an operational mode, and the contact tower is rotated down to be in a prostrated position relative to the base frame in a transportation mode.

BRIEF DESCRIPTION OF THE DRAWINGS

While certain embodiments will be described in connection with the illustrative embodiments shown herein, the invention is not limited to those embodiments. On the contrary, all alternatives, modifications, and equivalents are included within the spirit and scope of the invention as defined by the claims. In the drawing figures, which are not to scale, the same reference numerals are used throughout the description and in the drawing figures for components and elements having the same structure, and primed reference numerals are used for components and elements having a similar function and construction to those components and elements having the same unprimed reference numerals.

DETAILED DESCRIPTION

Figure 1:
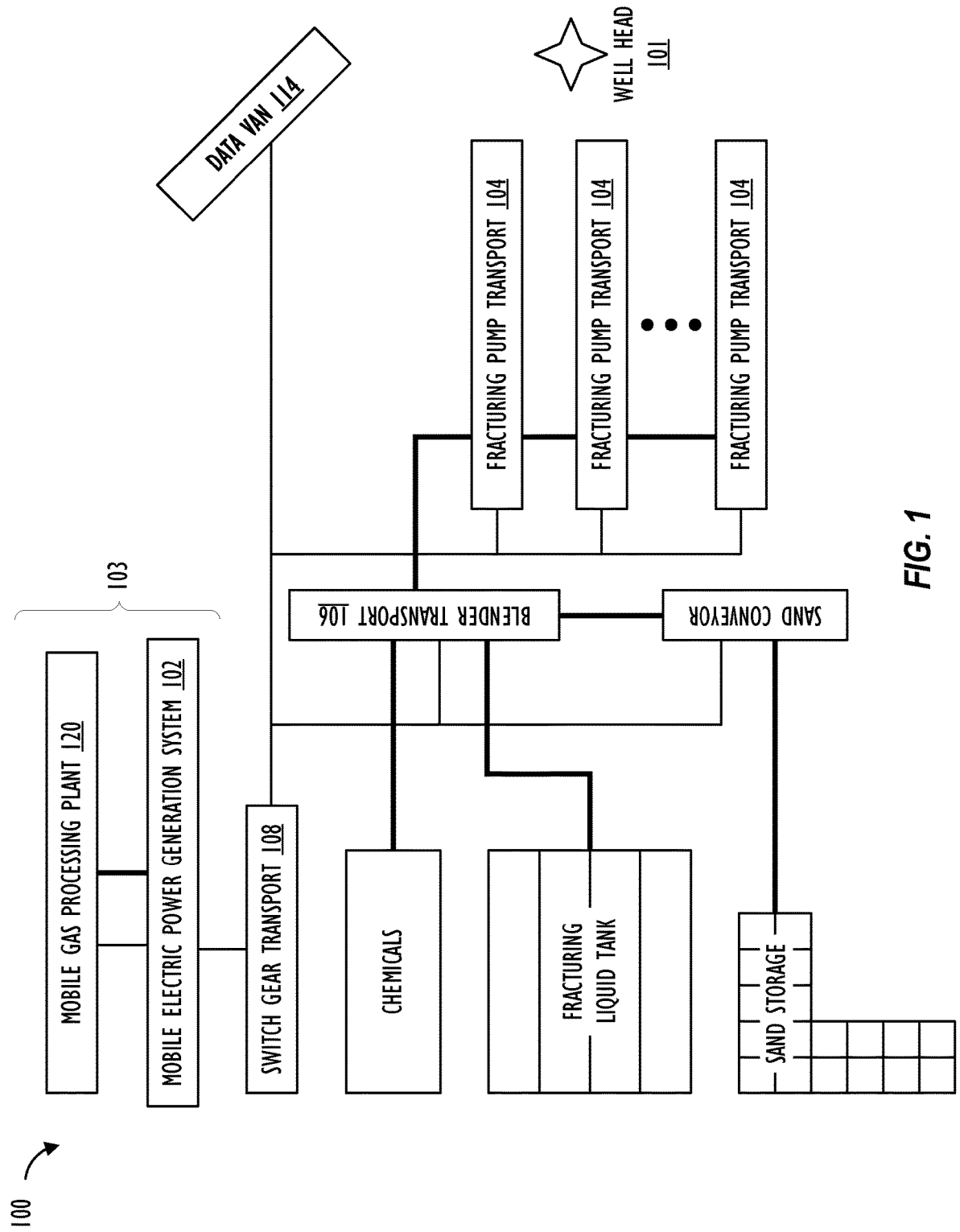
FIG. 1 is a schematic diagram of a well site that comprises a wellhead and a mobile fracturing system in accordance with one or more embodiments.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts or suffixes are understood to reference all instance of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

The terms "a," "an," and "the" are not intended to refer to a singular entity unless explicitly so defined, but include the general class of which a specific example may be used for illustration. The use of the terms "a" or "an" may therefore mean any number that is at least one, including "one," "one or more," "at least one," and "one or more than one." The term "or" means any of the alternatives and any combination of the alternatives, including all of the alternatives, unless the alternatives are explicitly indicated as mutually exclusive. The phrase "at least one of" when combined with a list of items, means a single item from the list or any combination of items in the list. The phrase does not require all of the listed items unless explicitly so defined.

As used herein, the term "transport" refers to any assembly, including, but not limited to, a trailer, truck, skid, rail car, and/or barge used to transport relatively heavy structures and/or other types of articles, such as fracturing equipment and fracturing sand. A transport could be independently movable from another transport. For example, a first transport can be mounted or connected to a motorized vehicle that independently moves the first transport while an unconnected second transport remains stationary.

As used herein, the term "trailer" refers to a transportation assembly used to transport relatively heavy structures and/or other types of articles (such as fracturing equipment and fracturing sand) that can be attached and/or detached from a transportation vehicle used to pull or tow the trailer. As an example, the transportation vehicle is able to independently move and tow a first trailer while an unconnected second trailer remains stationary. In one or more embodiments, the trailer includes mounts and manifold systems to connect the trailer to other fracturing equipment within a fracturing system or fleet. As used herein, the term "lay-down trailer" refers to a trailer that includes two sections with different vertical heights. One of the sections or the upper section is positioned at or above the trailer axles and another section or the lower section is positioned at or below the trailer axles. In one embodiment, the main trailer beams of the lay-down trailer may be resting on the ground when in operational mode and/or when uncoupled from a transportation vehicle, such as a tractor.

This disclosure pertains to a mobile gas processing plant and method for processing (e.g., cleaning, purifying, drying, filtering, heating, conditioning, and the like) a hydrocarbon gas mixture with the mobile gas processing plant to generate purified hydrocarbon gas (e.g., purified natural gas or hydrocarbon gas, dry natural gas, sales quality gas) that can be used to fuel a mobile electric power generation system. Components of the mobile gas processing plant are fixedly and permanently mounted on one or more mobile transports. In one embodiment, the mobile gas processing plant includes components that are mounted on a base frame of a transport and that include an inlet, an emergency shutdown device (ESD), a first Joule-Thomson (JT) valve unit, an inlet scrubber, an inlet filter separator, a dual pass line heater, a Triethylene Glycol (TEG) dehydration unit, a second JT valve unit, a vertical separator, an outlet filter separator, an outlet, and a control unit. The mobile gas processing plant is capable of handling as input, a wide quality range of hydrocarbon gas (e.g., raw or unprocessed hydrocarbon gas, partially processed hydrocarbon gas) that may include a variety of impurities, contaminants, and higher molecular mass hydrocarbons. From the input raw or partially processed hydrocarbon gas, the mobile gas processing plant can produce pipeline quality dry natural gas that is suitable for use by the mobile electric power generation system without further processing. Further, the mobile gas processing plant is adapted for quick mobilization and demobilization without requiring re-piping between the permanently installed components of the mobile plant. That is, the mobile gas processing plant can be quickly and easily switched between a transportation mode suitable for transportation of the mobile gas processing plant from site-to-site, and an operational mode in which the mobile gas processing plant processes an input hydrocarbon gas mixture to generate purified hydrocarbon gas (e.g., sales quality dry natural gas).

Conventional gas processing systems may include multiple layers of filtration and heating to generate sales quality natural gas. However, such conventional systems are not mobile and they require use of four or more trailers to transport ground-based skids from site-to-site to provide the necessary gas processing capability for generating sales quality gas for use as fuel by a gas turbine. Further, since such conventional systems carry ground-based equipment from site-to-site on separate (four or more) trailers, after reaching each location, the conventional systems require manual rigging in of the piping to interconnect the components of the ground-based skids to achieve an operational state. In summary, the conventional systems are not mobile, and require significant time, human effort, equipment, and cost to mobilize and demobilize the gas processing operation from site-to-site. The conventional systems also have a much larger site footprint.

By contrast, techniques disclosed herein look to provide a gas processing capability that is fully mobile with components for gas processing that are permanently installed, interconnected, condensed, and packaged into a single transport (or two or more transports), and that can be quickly moved from site-to-site, and can begin operation without requiring any additional piping or interconnection of the various components. Further, the mobile gas processing plant according to the present disclosure is able to handle any available quality of the hydrocarbon gas mixture as input, is able to process the input gas mixture, and generate fully processed hydrocarbon gas that is clean, dry and of sales quality, and is ready for use as fuel for a gas turbine. The mobile gas processing system is capable not only to strip liquids from the input hydrocarbon gas mixture, but also separate and remove higher molecular mass hydrocarbons, and generate gas that is pure strength and of sales quality. The system and method according to the present disclosure is thus able to produce the same quality of output hydrocarbon gas as conventional systems, while, unlike the conventional systems, also being fully mobile, having a much smaller on-site footprint, and having significantly lower mobilization and demobilization times, and resulting lower time, human effort, and cost requirements. Further, unlike conventional systems, the system and method according to the present disclosure also requires less piping and less turns, which results in less pressure loss. Since components of the mobile gas processing plant according to the present disclosure are permanently mounted, it does not need to be rigged up after reaching the location, or rigged down, and is ready for operation simply by driving the trailer to the location, and connecting an inlet, an outlet, and drain lines.

The mobile gas processing plant according to the present disclosure is designed to handle any quality hydrogen gas mixture. In applications with a high concentration of hydrogen sulfide, an amine unit to neutralize and/or remove hydrogen sulfide from the gas stream may be installed upstream of the mobile gas processing plant so that the input hydrogen gas mixture has hydrogen sulfide concentration that is not above acceptable limits. And in this case, any condensation or moisture that was created and added to the gas mixture by the amine unit will be removed by the processing on board the mobile gas processing plant so that what flows out of the mobile gas processing plant is clean, dry, sales quality natural gas.

FIG. 1 is a schematic diagram of an embodiment of a well site that comprises wellhead 101 and mobile fracturing system 100. Generally, mobile fracturing system 100 may perform fracturing operations to complete a well and/or transform a drilled well into a production well. For example, the well site may be a site where operators are in the process of drilling and completing a well. Operators may start the well completion process with vertical drilling, running production casing, and cementing within the wellbore. The operators may also insert a variety of downhole tools into the wellbore and/or as part of a tool string used to drill the wellbore. After the operators drill the well to a certain depth, a horizontal portion of the well may also be drilled and subsequently encased in cement. The operators may subsequently pack the rig and move mobile fracturing system 100 onto the well site to perform fracturing operations that force relatively high pressure fracturing fluid through wellhead 101 into subsurface geological formations to create fissures and cracks within the rock. Mobile fracturing system 100 may then be moved off the well site once the operators complete fracturing operations. Typically, fracturing operations for well site may last several days.

FIG. 1 illustrates that mobile fracturing system 100 includes multiple fracturing pump transports 104 and hydration-blender transport 106. Switch gear transport 108 directly provides the hydration-blender transport 106 and fracturing pump transports 104 electric power at a relatively higher-medium voltage level (e.g., 13.8 kilovolts (kV)). Prime movers, and drives (e.g., variable frequency drives (VFDs)) to control and monitor the prime movers, are disposed on transports 104 and 106, and transformers for stepping down voltage levels are mounted on transports 104 and 106. For example, each fracturing pump transport 104 has a transformer that steps down the input voltage (e.g., 13.8 kV) to one or more different voltages (e.g., 4.2 kV, 600 volts (V), 480 V). Hydration-blender transport 106 may also have its own transformer to step down the input voltage to one or more voltage levels. Hydration-blender transport 106 may also provide electric power at the stepped down to one or more lower voltage levels (e.g., 4.2 kV, 600 V, 480 V) to other downstream fracturing equipment, such as a sand conveyor.

In FIG. 1, mobile fracturing system 100 includes mobile source of electricity 103 that includes mobile electric power generation system 102 and mobile gas processing plant 120 (e.g., mobile gas processing transport). Mobile electric power generation system 102 is configured to generate electricity to supply to fracturing pump transports 104, hydration-blender transport 106, data van 114, and/or other fracturing equipment at the well site. FIG. 1 illustrates that mobile electric power generation system 102 is a centralized power generation system that distributes power to most or all of the fracturing equipment within mobile fracturing system 100. As an example, mobile electric power generation system 102 is able to produce electric power in the range of about 5-50 megawatts (MW) to perform hydraulic fracturing operations at a well site with one or more wells. In one embodiment, mobile electric power generation system 102 includes a turbine-electric generator transport and an air inlet and exhaust transport. The turbine-electric generator transport compresses and mixes combustion air with (purified) hydrocarbon gas supplied by mobile gas processing plant 120 to spin and generate mechanical energy and then converts the mechanical energy to electricity. The inlet and exhaust transport provides ventilation and combustion air to the turbine-electric generator transport when generating electricity. In other embodiments, mobile electric power generation system 102 may include a single transport, or may include three or more transports. Regardless of the number of transports, mobile electric power generation system 102 includes at least the gas turbine that uses the purified hydrocarbon gas from the mobile gas processing plant 120 as fuel to generate mechanical energy, and the generator that uses the mechanical energy to generate electricity.

To generate electric power, mobile source of electricity 103 utilizes hydrocarbon gas (e.g., natural gas) obtained from a hydrocarbon fuel source. The hydrocarbon fuel source may be a hydrocarbon gas line available at a well site that contains hydrocarbon gas from one or more producing wellheads and/or pipelines and/or gathering systems, where the hydrocarbon gas may be (raw) unprocessed or partially processed when input to mobile source of electricity 103. For example, the hydrocarbon gas line may be part of the wellhead flowline that carries unprocessed hydrocarbon gas that contains not only the useable hydrocarbon gas, but also water, sand, and other contaminants, impurities, and higher molecular mass hydrocarbons. As another example, the hydrocarbon gas line may be downstream of a gathering and sales pipeline where the hydrocarbon gas has been partially processed to neutralize and/or remove hydrogen sulfide from the gas stream so that the level of hydrogen sulfide in the hydrocarbon gas line is below a preset limit.

Although FIG. 1 describes mobile source of electricity 103 as being part of mobile fracturing system 100 for performing electric hydraulic fracturing operations at well head 101, mobile source of electricity 103 is not limited to hydraulic fracturing operations, but may be used for any application where mobile electric power is needed. For example, mobile source of electricity 103 may be implemented to provide mobile electric power for other applications (e.g., industrial, mining, commercial, civilian, agricultural, manufacturing, and the like) where such mobile electric power is needed and where the requisite hydrocarbon fuel (e.g., dry, sales quality natural gas) required to fuel the power generation transport is available. Mobile source of electricity 103 may be configured to be transportable to different locations. Once mobile source of electricity 103 is no longer required at a given location, it may be easily transported to a new location where it is now required.

As shown in FIG. 1, mobile source of electricity 103 includes mobile gas processing plant 120 to treat (e.g., process, purify, condition, clean, and the like) the raw or partially processed hydrocarbon gas mixture supplied from the hydrocarbon fuel source and to output purified hydrocarbon gas (e.g., natural gas) that meets predetermined quality standards for use by the gas turbine of mobile electric power generation system 102. In one or more embodiments, because of mobility restrictions, mobile power generation plant 120 could be a trailer with limited width, length, and height dimensions. As an example, to comply with certain roadway restrictions, the trailer may have a maximum width of about 8 feet and 6 inches and a maximum length of about 59 feet. Based on the trailer dimensions, the amount of trailer space to mount components of mobile power generation plant 120 may be limited. Further, mobile gas processing plant 120 may mount components thereof on a laydown trailer with at least three axles used to support and distribute the weight. Other embodiments of mobile gas processing plant 120 may be a trailer that exceeds three axles depending on the total transport weight. The dimensions and the number of axles may be adjusted to allow for the transport over roadways that typically mandate certain height, length, and weight restrictions.

Figure 2:
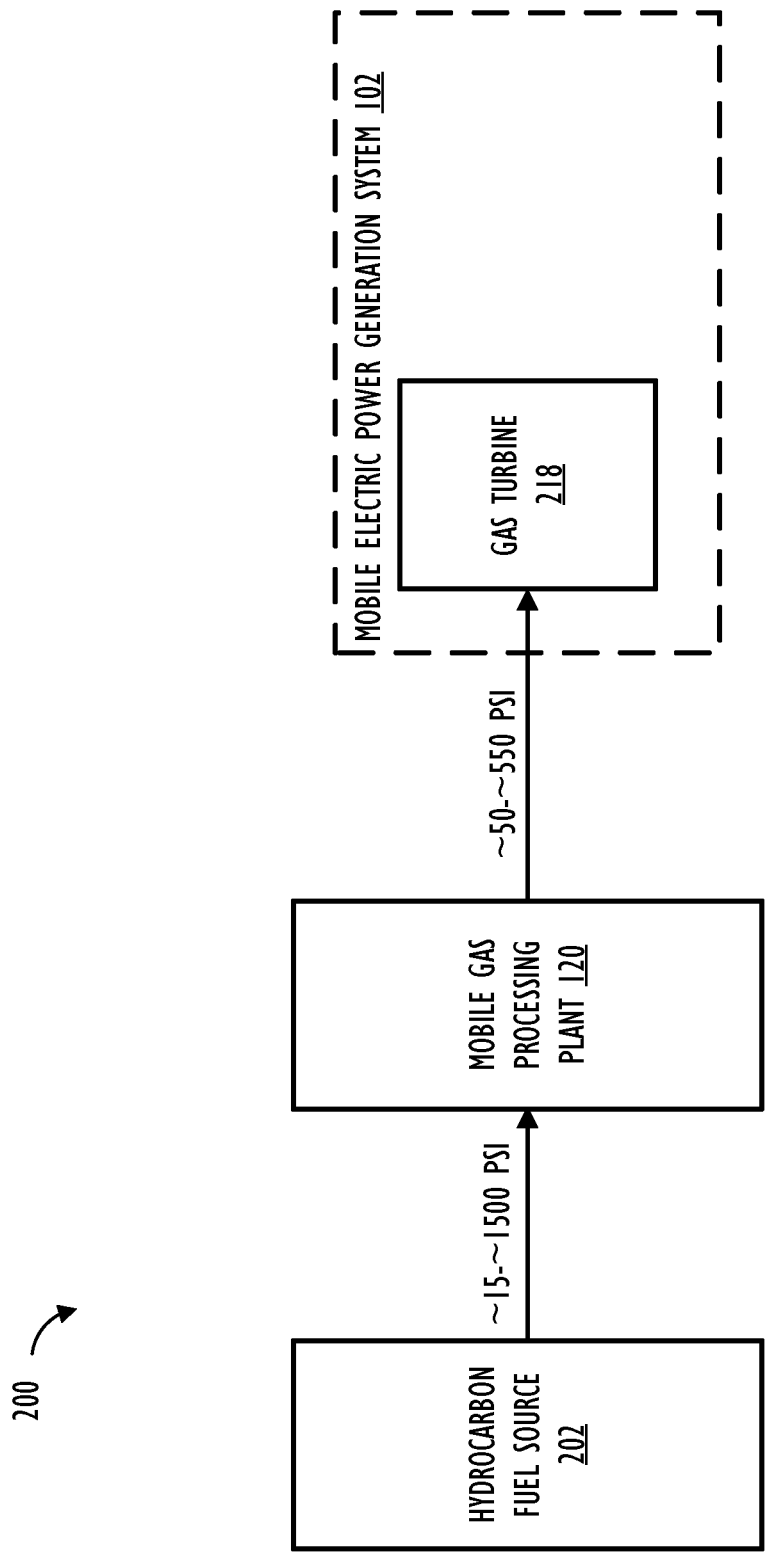
FIG. 2 is a block diagram of a gas flow path that supplies hydrocarbon gas to a gas turbine within a mobile electric power generation system in accordance with one or more embodiments.

FIG. 2 is block diagram 200 of a gas flow path that supplies hydrocarbon gas to gas turbine 218 within mobile electric power generation system 102. The gas flow path starts with hydrocarbon fuel source 202 supplying the raw or partially processed hydrocarbon gas mixture to mobile gas processing plant 120. As explained previously, hydrocarbon fuel source 202 may be a hydrocarbon gas line that supplies unprocessed and/or partially processed hydrocarbon field gas mixture from a producing wellhead and/or from gathering systems and/or other upstream pipelines. The hydrocarbon fuel source 202 may supply the hydrocarbon gas mixture to mobile gas processing plant 120 at pressures ranging from about 15 PSI to about 1500 PSI. Mobile gas processing plant 120 treats the received raw or unprocessed hydrocarbon gas mixture to generate processed hydrocarbon gas (e.g., purified or dry natural gas, sales quality natural gas, and the like) that gas turbine 218 of mobile electric power generation system 102 is able to directly use as fuel for power conversion.

More specifically, in FIG. 2, the hydrocarbon gas received from hydrocarbon fuel source 202 by mobile gas processing plant 120 may be a gas mixture that is raw, unprocessed, or partially processed, and that includes one or more hydrocarbon-based gases, other types of gases, impurities and/or contaminants. For example, the gas mixture may include varying amounts of: methane; ethane; higher molecular mass hydrocarbons including heavier gaseous hydrocarbons or Natural Gas Liquids (NGLs)) like propane, butane, and pentanes; ethylene, and liquid hydrocarbons like natural gasoline or crude oil; acid gases like carbon dioxide, carbon monoxide, hydrogen sulfide, and mercaptans; other gases like nitrogen and helium; liquid water; water vapor; dissolved salts and dissolved gases; sand and other solid impurities and/or contaminants; mercury; and the like.

On the other hand, gas turbine 218 in FIG. 2 may be configured to operate using hydrocarbon gas (e.g., dry or sales quality natural gas) that has been purified, cleaned, and/or conditioned to meet predetermined quality standards. For example, the hydrocarbon gas input to operate gas turbine 218 may be dry natural gas that has been generated by mobile gas processing plant 120 performing processing on the hydrocarbon gas mixture from source 202 to remove higher molecular mass hydrocarbons, other gases, liquids, airborne particulates, and other impurities and/or contaminants, thereby purifying the gas mixture to meet predetermined quality standards and generate pure strength gas. For example, hydrocarbon gas mixture input to mobile gas processing plant 120 from source 202 in FIG. 2 may be approximately 1300-1350 BTUs. After processing (e.g., stripping, cleaning, conditioning, purifying) at mobile gas processing plant 120, the dry natural gas that may be output to gas turbine 218 may be approximately 1000-1100 BTUs.

In FIG. 2, mobile gas processing plant 120 directs processed hydrocarbon gas (e.g., cleaned natural gas) to gas turbine 218 at a designated pressure level that may be in the range of approximately 50-550 PSI. The designated pressure level for the output hydrocarbon gas could be set depending on the design requirements of gas turbine 218. As an example, the General Electric® 2500 gas turbine may utilize hydrocarbon gas at pressures ranging from about 500 PSI to about 550 PSI, and in this case, mobile gas processing plant 120 may be set to direct cleaned natural gas to gas turbine 218 at around 525 PSI. Other gas turbines may utilize hydrocarbon gas at varying pressure levels, for example, about 150 PSI to about 400 PSI, and mobile gas processing plant 120 may be set accordingly. Mobile gas processing plant 120 and method of operation thereof is discussed in more detail with reference to FIGS. 3-10 below.

Although FIG. 3-7 illustrate mobile gas processing plant 120 as a plant whose components are permanently mounted on a single mobile transport (e.g., trailer), in other embodiments, mobile gas processing plant 120 may be a plant whose gas processing equipment is permanently mounted on two or more mobile transports. Regardless of the number of transports, mobile gas processing plant 120 is configured as a mobile unit with permanently installed components that are adapted for quick mobilization and demobilization from site-to-site without requiring re-piping between the permanently installed components. That is, mobile gas processing plant 120 shown in FIGS. 3-7 can be quickly converted from a transportation mode (FIG. 7) to an operational mode (FIG. 6) by connecting an inlet hydrocarbon gas mixture line, an outlet dry or cleaned gas line, and a drain line, and (optionally) positioning a contact tower of dehydration unit 330 in a vertical position.

As shown in FIGS. 3-7, mobile gas processing plant 120 may include a variety of components the perform gas processing operations on the input hydrocarbon gas mixture. The operations performed by the components of mobile gas processing plant 120 on the gas mixture may include, but are not limited to, regulating hydrocarbon gas pressures and temperatures, heating the hydrocarbon gas mixture, separating out liquids (e.g., higher molecular mass hydrocarbons, water) from the hydrocarbon gas mixture, filtering out unwanted impurities and contaminants (e.g., sand, airborne particulates, other impurities and/or contaminants) from the hydrocarbon gas mixture, and compressing the hydrocarbon gas. In one or more embodiments, the plurality of components installed on mobile gas processing plant 120 include inlet 305, Emergency Shutdown Device (ESD) 310, inlet scrubber 315, first Joule-Thomson (JT) valve unit 320, inlet filter separator 325, dehydration unit 330, tower receptacle 331, Triethylene Glycol (TEG) regen skid 332, second JT valve unit 335, vertical separator 340, outlet filter separator 345, outlet 350, dual pass line heater 360, and control unit 370. Mobile gas processing plant 120 may also include other components not specifically shown in the figures like compressors, transformers, and generators.

FIGS. 3-7 also illustrate that the different components of mobile gas processing plant 120 may be supported by being mounted on engineered base frame 405. Engineered base frame 405 (e.g., base frame, a sub-base, sub-skid, or any other sub-structure of trailer beams of plant 120) may be used to mount and align the connections between the various components. In the operational mode, engineered base frame 405 of mobile gas processing plant 120 may be supported on the ground by hydraulic legs 410 or may directly rest on the ground. Hydraulic legs 410 may comprise support feet and hydraulic cylinders that lift mobile gas processing plant 120 to a designated position. FIGS. 3-7 also illustrate that mobile gas processing plant 120 utilizes a lay-down trailer to enhance mobility, improved safety, and enhance ergonomics for crew members when performing routine maintenance and operations on the various components installed on plant 120. The lay-down trailer positions components of plant 120 closer to the ground as the main trailer beams are resting on the ground in operational mode. With the lay-down trailer design, mobile gas processing plant 120 has an upper section above the trailer axles that may hold or have mounted at least inlet 305, ESD 310, inlet scrubber 315, and first JT valve unit 320.

As shown in FIGS. 3-7, components of mobile gas processing plant 120 may be permanently installed so that mobile gas processing plant 120 can be transported from site-to-site without having to re-pipe or interconnect the various components and thus providing a "plug-and-play" solution for mobile gas processing, even in applications where the available hydrocarbon gas mixture for input is of low-quality (e.g., the gas mixture includes higher molecular mass hydrocarbons, other non-hydrocarbon gases, liquids, particulates, and other impurities and contaminants). Structure, function and operation of the various components of mobile gas processing plant 120 are described below with reference to FIGS. 8-10.

Figure 8:
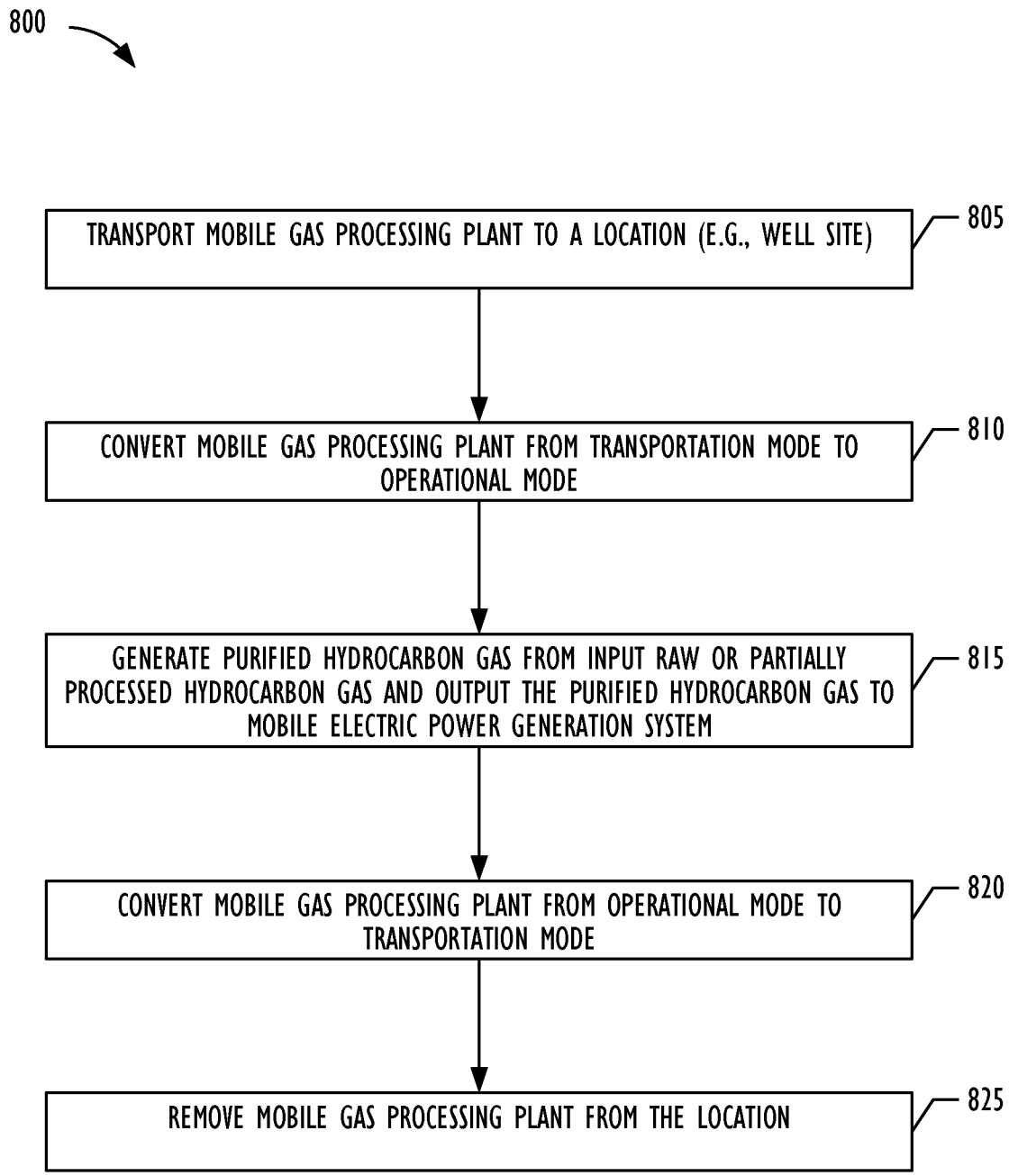
FIG. 8 is a flow chart of a method for providing a mobile gas processing plant for a mobile electric power generation system in accordance with one or more embodiments.

FIG. 8 is a flow chart of method 800 for providing mobile gas processing plant 120 for mobile electric power generation system 102 in accordance with one or more embodiments. Method 800 may begin at block 805 by transporting mobile gas processing plant 120 to a location. The location may be where mobile electric power generation by system 102 is needed to generate mobile electric power. For example, the location may be a well site (e.g., FIG. 1) where mobile electric power is needed to power hydraulic fracturing operations, and where hydrocarbon gas to fuel mobile electric power generation system 102 needs to be processed by operating mobile gas processing plant 120 before inputting the hydrocarbon gas to mobile electric power generation system 102.

Figure 6:
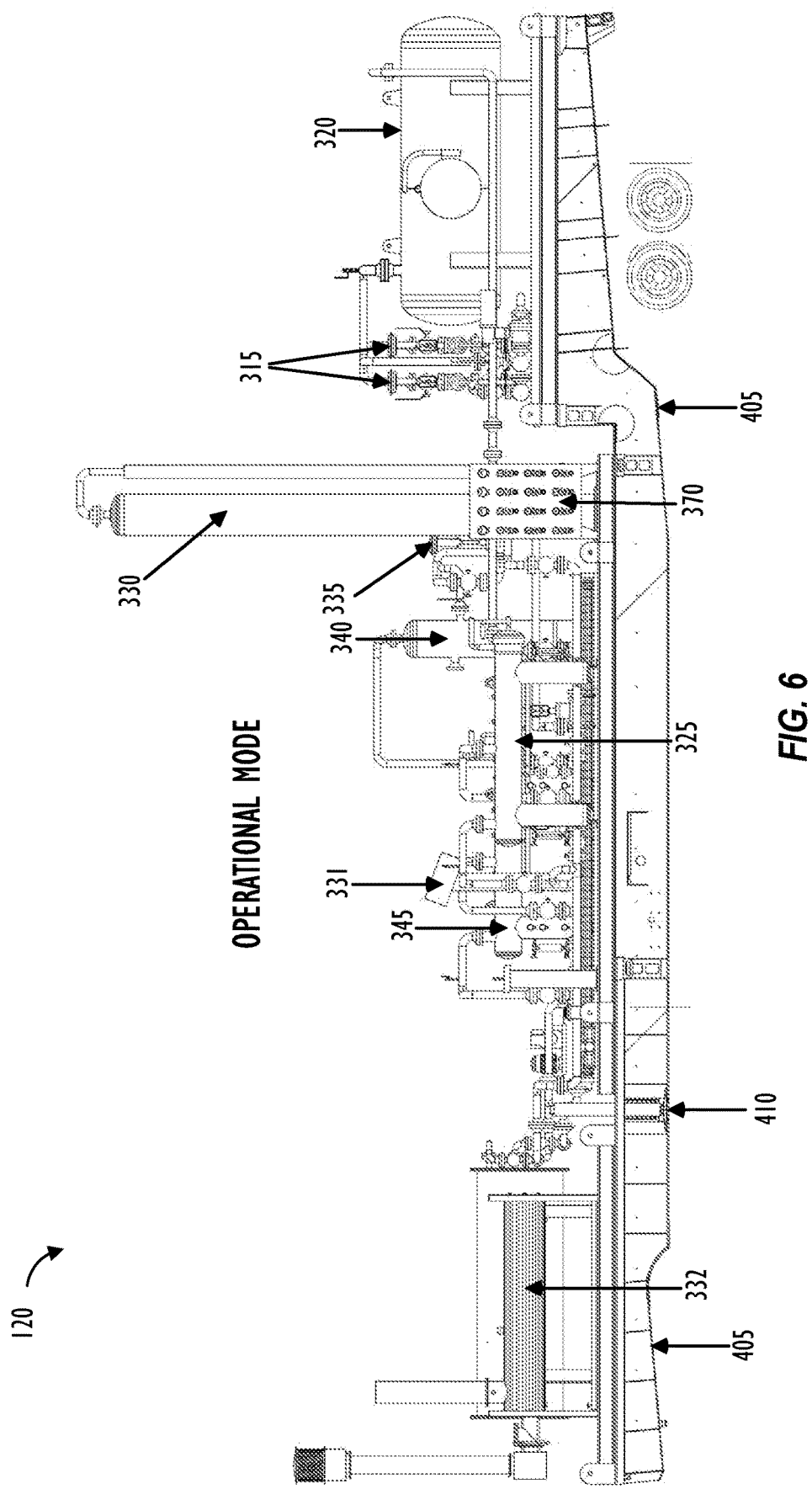
FIG. 6 is a profile view of a mobile gas processing plant in an operational mode in accordance with one or more embodiments.

Method 800 may then move to block 810, where mobile gas processing plant 120 is converted from a transportation mode to an operational mode. The same transport 120 may be used during the conversion from the transportation mode to the operational mode. In other words, transports other than transport 120 are not added and/or removed when setting up the mobile gas processing plant. Additionally, method 800 may be performed without the use of a forklift, crane, and/or other external mechanical means to transition mobile gas processing plant 120 into the operational mode. For example, at block 810, mobile gas processing plant 120 may be converted from transportation mode to operational mode by connecting inlet 305 to a hydrocarbon gas line (e.g., line of source 202 of FIG. 2) at the remote location of block 805, connecting outlet 350 of mobile gas processing plant 120 to a fuel inlet of mobile electric power generation system 102 (e.g., fuel inlet of turbine 218 of FIG. 2), connecting a drain line of mobile gas processing plant 120 to a storage or other pipeline, and positioning dehydration unit 330 from a horizontal position (FIG. 7; transportation mode; prostrated position) to a vertical position (FIG. 6; operational mode; upright position).

Figure 7:
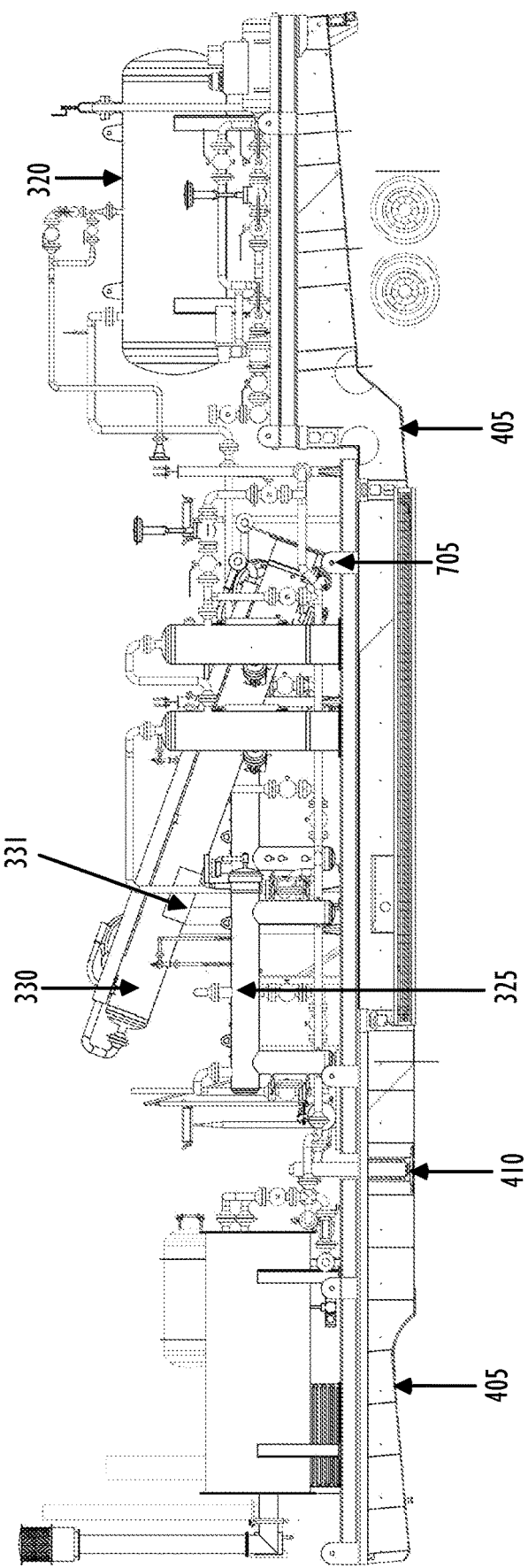
FIG. 7 is a profile view of a mobile gas processing plant in a transportation mode in accordance with one or more embodiments.

As shown in FIG. 7, dehydration unit 330 may be initially mounted on base frame 405 to lie on its side during transportation mode such that a top portion of dehydration unit 330 rests on tower receptacle 331. In the operational mode, dehydration unit 330 may be rotated up without using external mechanical means such that dehydration unit 330 no longer rests on receptacle 331 and such that dehydration unit 330 is mounted to frame 405 on its base and in the upright position. In the operational mode, dehydration unit 330 may be rotated from a horizontal position (FIG. 7) to a vertical position (FIG. 6) using hydraulics, pneumatics, and/or electric motors. As shown in FIG. 7, dehy unit 330 may be mounted on and connected to base frame 405 via hinge 705 such that dehy unit 330 is rotatable relative to base frame 405. The steps at block 810 to convert mobile gas processing plant 120 from transportation mode to the operational mode may be performed without requiring any mechanical apparatus external to transport 120.

Method 800 may then move to block 815 where the (raw or partially processed) hydrocarbon gas mixture input to mobile gas processing plant 120 is processed (e.g., purified, cleaned, conditioned) by the various components installed on mobile gas processing plant 120, and is output to mobile electric power generation system 120 as purified or dry hydrocarbon gas. Details of the operations performed at block 815 are described below in connection with FIGS. 9 and 10.

Method 800 may then move to block 820, where mobile gas processing plant 120 is converted from the operational mode to the transportation mode without utilizing any external mechanical apparatus. Similar to block 810, the conversion process for block 820 may use the same transport without using a forklift, crane, and/or other external mechanical means to transition mobile gas processing plant 120 back to the transportation mode. For example, at block 820, mobile gas processing plant 120 may be converted to transportation mode from operational mode by disconnecting inlet 305 from the hydrocarbon gas line at the remote location of block 805, disconnecting outlet 350 of mobile gas processing plant 120 from the fuel inlet of mobile electric power generation system 102, disconnecting the drain line of mobile gas processing plant 120 from the storage or other pipeline, and positioning dehydration unit 330 from the vertical position (FIG. 6) to the horizontal position (FIG. 7). Method 800 may then move to block 825 to remove mobile gas processing plant 120 from the location after mobile gas processing and mobile electric power generation is no longer needed at the location.

Figure 9:
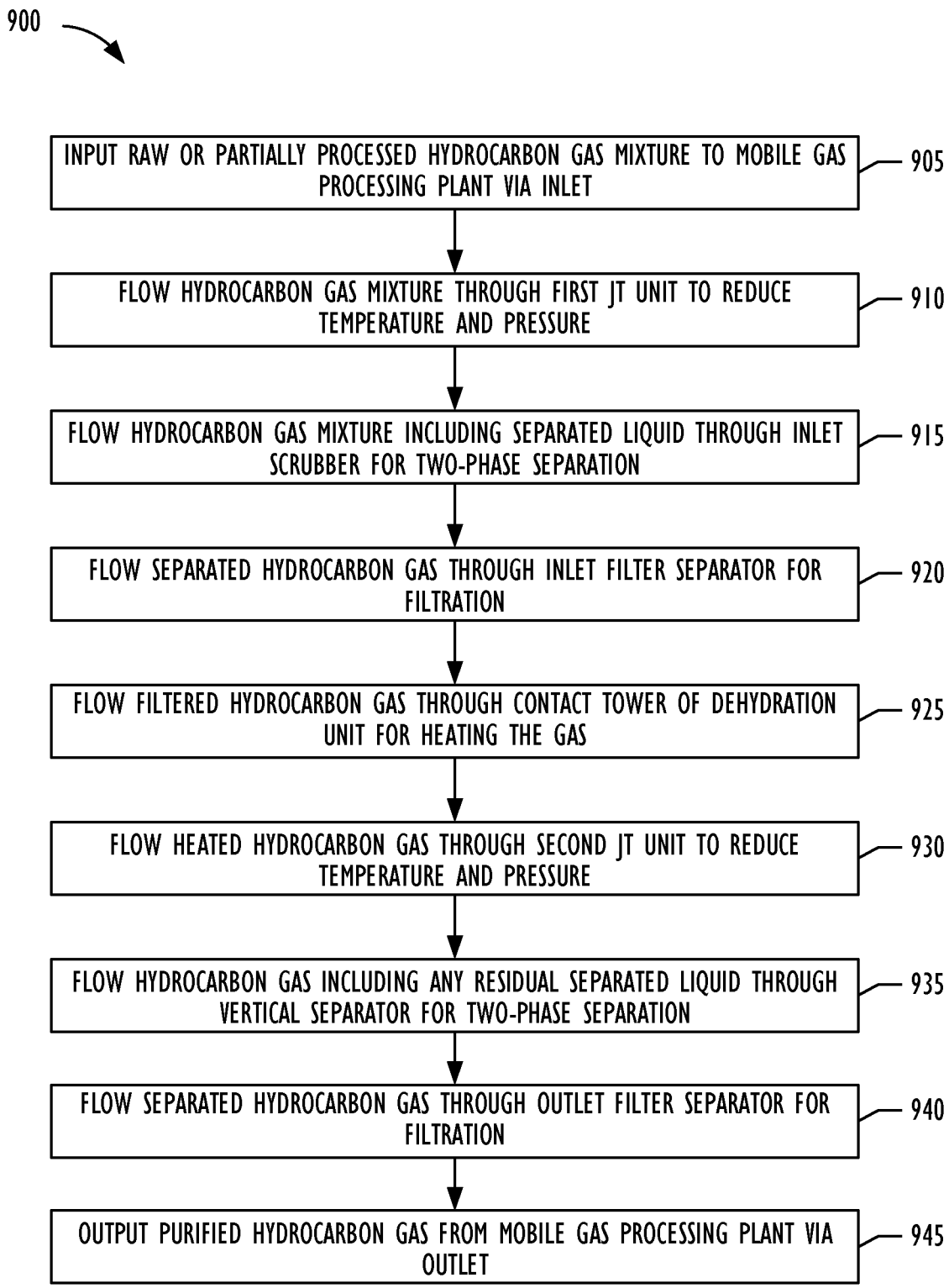
FIG. 9 is a flow chart illustrating a method for processing input hydrocarbon gas mixture with a mobile gas processing plant.

FIG. 9 is a flow chart illustrating method 900 for processing input hydrocarbon gas mixture with mobile gas processing plant 120. Method 900 is performed by mobile gas processing plant 120 after the plant is in the operational mode (e.g., Block 815 of FIG. 8). Although FIG. 9 illustrates that blocks of method 900 are implemented in a particular sequential order of operations, method 900 is not limited to this order of operations, and instead other embodiments of method 900 may have one or more blocks implemented in a different order, one or more blocks omitted, and/or one or more blocks replaced with other blocks.

Figure 3:
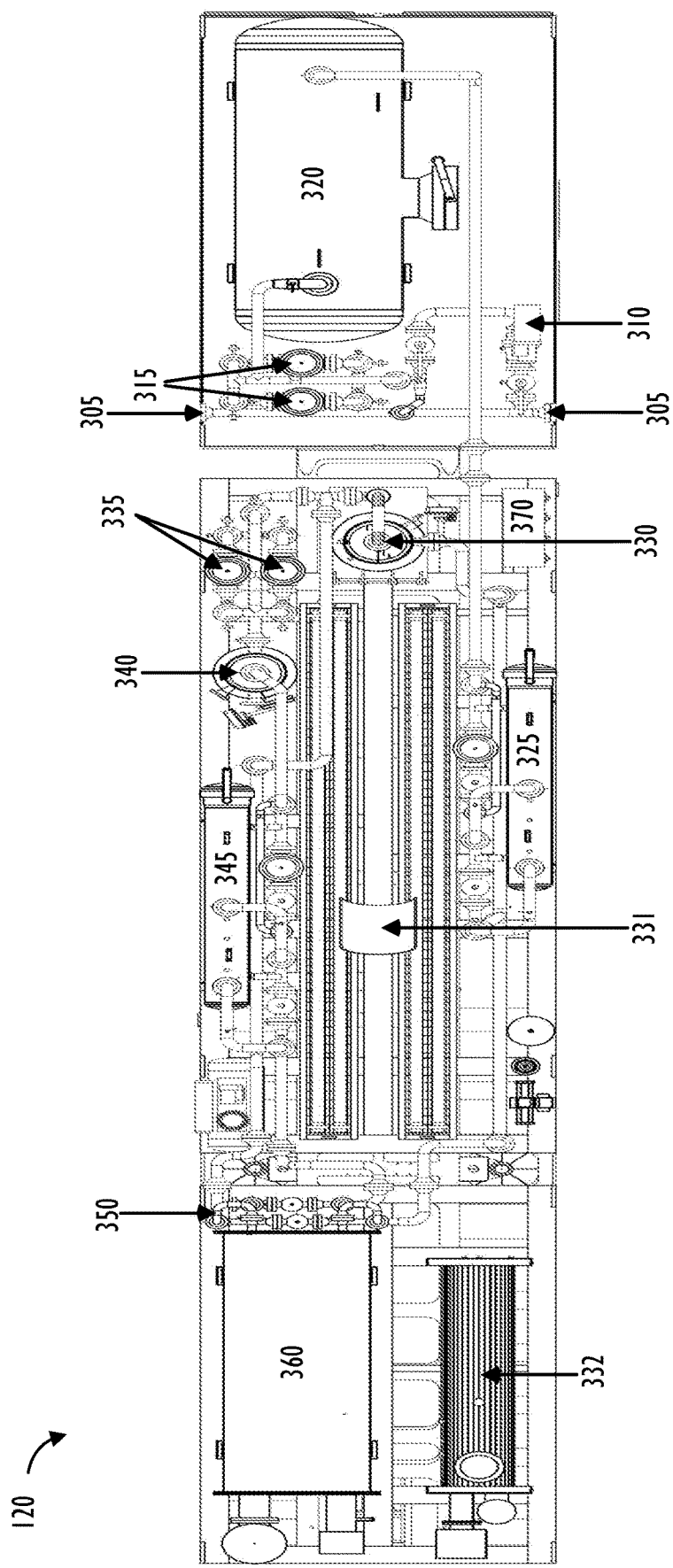
FIG. 3 is a plan view of a mobile gas processing plant in accordance with one or more embodiments.
Figure 4:
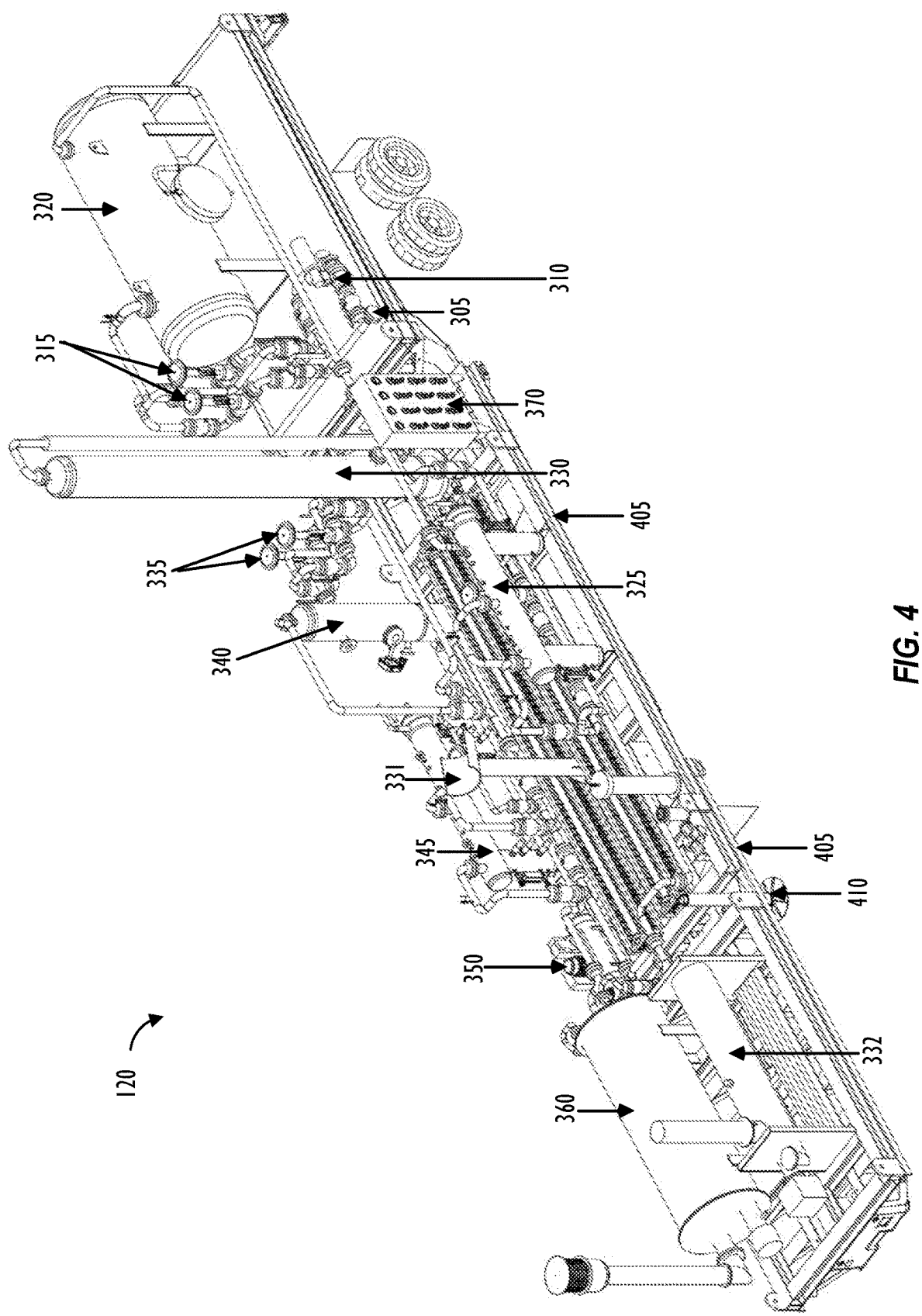
FIGS. 4 and 5 are different perspective views of a mobile gas processing plant in accordance with one or more embodiments.
Figure 5:
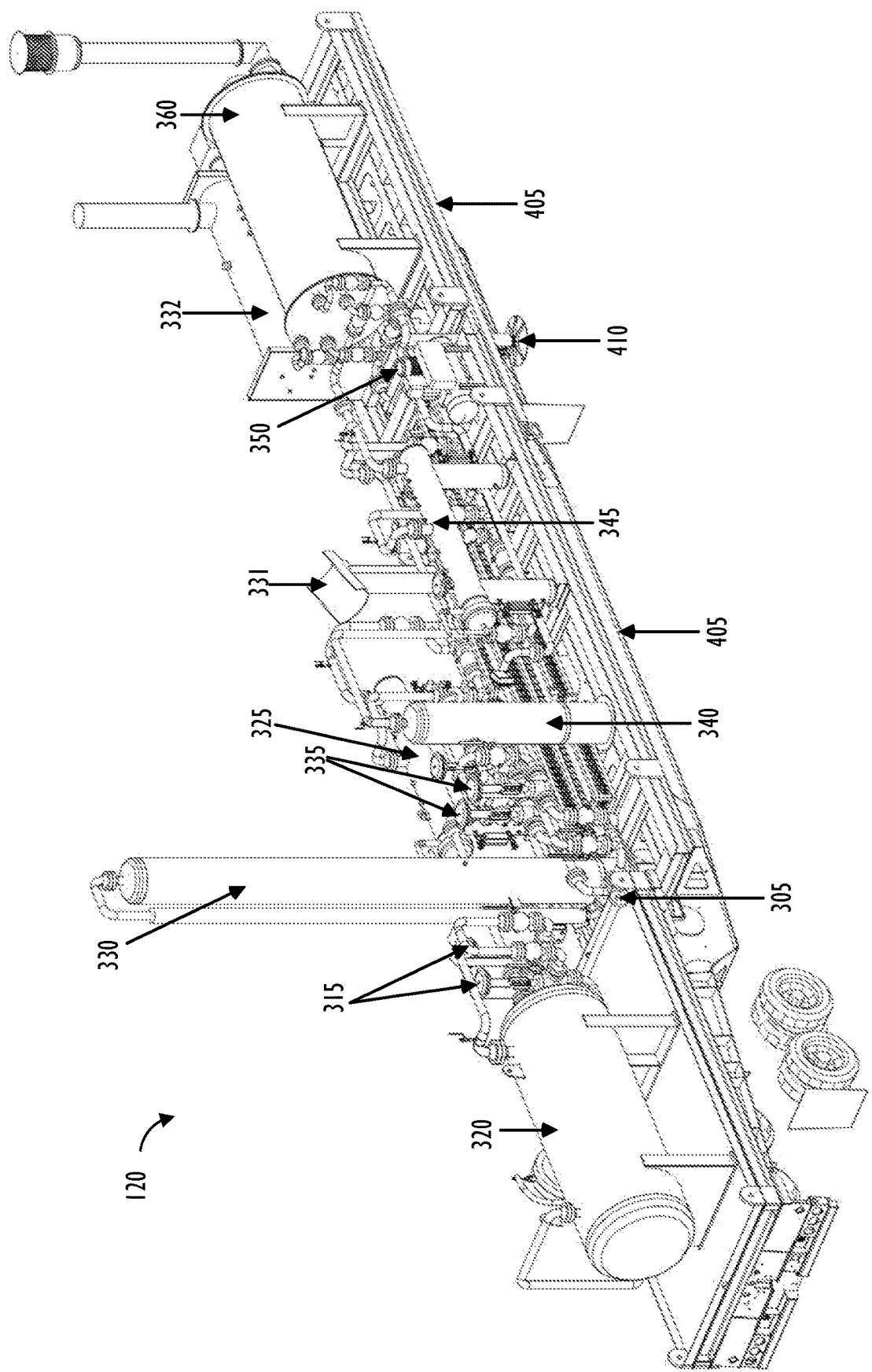

Method 900 begins at block 905 where the hydrocarbon gas mixture (e.g., gas mixture from source 202 of FIG. 2) is input to mobile gas processing plant 120 for processing. In the embodiment shown in FIGS. 3-7, at block 905, the raw or partially processed hydrocarbon gas mixture from the hydrocarbon gas line at the location where the gas processing operations are to be performed is input to inlet 305 of mobile gas processing plant 120. Inlet 305 may be an inlet header that is adapted to connect to the hydrocarbon gas line that supplies the unprocessed and/or partially processed hydrocarbon field gas from a producing wellhead and/or from gathering systems and/or other upstream pipelines. As shown in FIG. 3, inlet header 305 may be provided on both longitudinal sides of mobile gas processing plant 120 for ease of connectivity. At block 905, the input gas mixture flowing in from inlet 305 may then pass through ESD 310 that is installed on mobile plant 120. ESD 310 is an emergency shutdown device that is configured to monitor inlet pressure and protect equipment installed on mobile plant 120 from excessively high pressures. Thus, in the event the inlet pressure of the gas input at block 905 goes above a predetermined threshold pressure level (e.g., pressure level detected by a (analog or digital) sensor disposed at ESD 310 higher than a threshold), ESD 310 may automatically shutdown (e.g., using electronic controller, and actuators operating using hydraulics, pneumatics, electric motor, and the like) to prevent flow of the gas mixture flowing in from inlet header 305 to downstream components of plant 120.

Method 900 then proceeds to block 910 where the gas mixture stream flows through first JT unit 315 to reduce temperature and pressure of the hydrocarbon gas mixture. In the embodiment shown in FIGS. 3-7, at block 910, the hydrocarbon gas mixture that has flown past ESD 310 flows through first JT unit 315. First JT unit 315 may include at least two JT valves (or porous plugs). The first JT valve of first JT unit 315 (e.g., digital or electronic valve) may work as a primary valve and the second JT valve of first JT unit 315 (e.g., pneumatic valve) may work as a backup in the event the first JT valve fails. First JT unit 315 produces the Joule-Thomson effect on the hydrocarbon gas mixture passing therethrough by forcing the gas mixture through the (first or second) JT valve or porous plug thereof while keeping the gas mixture insulated so that no heat exchange occurs, thereby causing a temperature drop and a pressure drop (e.g., pressure cut) of the gas mixture. Dropping the pressure of the gas mixture and its temperature causes most aerosol liquids (e.g., higher molecular mass hydrocarbons, water vapor, and the like) mixed in the gas mixture to drop below their dew points and turn into a solid liquid (e.g., NGLs, water, and the like). As a result, a portion of the hydrocarbon gas mixture may separate into liquids, thereby purifying (e.g., cleaning) the hydrocarbon gas.

The at least two JT valves of first JT unit 315 may be controlled by one or more of electronic, pneumatic, and hydraulic means to automatically set one of the at least two JT valves of first JT unit 315 to be in operation at a given time. Thus, during operation, if control unit 370 detects a trim or other problem on the first JT valve of JT unit 315 that is currently in operation, control unit 370 may automatically shut the first JT valve and switch the gas flow to pass through a second JT valve of JT unit 315, thereby ensuring continuous operation of first JT unit 315 without requiring shutdown of the whole system even in the event of a valve failure. By providing redundant JT valves having identical function, continuous operation of mobile plant 120 can be achieved even when a technician needs to repair or replace a malfunctioning JT valve. Control unit 370 may be configured to electronically or pneumatically control (e.g., using electronic or pneumatic actuators) the operation to shut the first JT valve and to switch the gas flow to pass through the second JT valve. For example, when a sensor of first JT unit 315 senses an interruption in signal or pressure drop that does not correspond with an inlet pressure, control unit 370 may control to close the first JT valve in operation while opening an inlet of the second JT valve automatically to steady the flow for operation without interruption. Thus, for example, at block 910, gas mixture stream that flows into first JT unit 315 at, e.g., 1000 psi, may be dropped down to around 250-300 psi by passing through the JT valve thereof, thereby causing the temperature and pressure of the gas mixture to drop, and as a result, increase in a proportion of free liquids (e.g., NGLs) and/or condensate in the gas mixture by going from a vaporized or aerosol form to a liquidized form.

Method 900 then proceeds to block 915 where the hydrocarbon gas mixture including the liquids separated at block 910 flow through inlet scrubber 320. In the embodiment shown in FIGS. 3-7, at block 915, the hydrocarbon gas mixture including the liquids separated by first JT unit 315 flow through inlet scrubber 320 for two-phase separation of the mixture. Inlet scrubber 320 is a two-phase separator vessel that will allow the gas portion of the hydrocarbon gas mixture stream to pass through, and catch and separate all of the liquids (e.g., NGLs (ethane, propane, butane, and the like), liquid water, and the like) in the stream, and transport the separated liquids to a designated pipeline or containment for removal. For example, removal of liquids in inlet scrubber 320 may be controlled by a series of liquid level switches and sensors that will empty out the separated liquids from inlet scrubber 320 to a drain line when a set level is reached.

Next, at block 920, the hydrocarbon gas stream separated at block 915 flows through an inlet filter separator. In the embodiment shown in FIGS. 3-7, at block 920, the hydrocarbon gas stream separated at inlet scrubber 320 flows through a flow path of inlet filter separator (e.g., coalescing unit) 325 for further processing (e.g., filtration, purification, cleaning) of the hydrocarbon gas. Even after separating liquids from the hydrocarbon gas mixture at inlet scrubber 320, the separated hydrocarbon gas stream may still include therein residual liquids in vaporized form, airborne particulates, and/or impurities and/or contaminants. That is, the separated hydrocarbon gas flowing out of inlet scrubber 320 may require additional processing to remove humidity and/or other particulates. Inlet filter separator 325 may include a first filter bank of one or more gas filters (or series of gas filters) set at predetermined micron levels (e.g., gas filters up to around 3-4 microns) to filter out particulates (e.g., elemental sulfurs, airborne particulates, and the like). As the hydrocarbon gas stream passes through the series of gas filters of the first filter bank of inlet filter separator 325, the hydrocarbon gas becomes further purified by removal of airborne condensate and particulate matter, and any additional liquids filtered out at inlet filter separator 325 may fall to a bottom or boot of inlet filter separator 325 and may be disposed in the same manner as the liquids removed at inlet scrubber 320. For example, the impurities filtered out by inlet filter separator 325 may be drained out via the drain line that is also coupled to inlet scrubber 320 for further downstream processing or disposal.

Next, at block 925, the hydrocarbon gas stream filtered at block 920 flows through a dehydration unit to heat and dehydrate the hydrocarbon gas. In the embodiment shown in FIGS. 3-7, at block 925, the hydrocarbon gas filtered and separated at inlet filter separator 325 flows through a flow path of dehydration unit 330 for further processing (e.g., heating, purification, cleaning). Dehydration unit 330 may be a Triethylene Glycol (TEG) dehydration unit (e.g., dehy unit) that includes a contact tower permanently mounted and mobilized on base frame 405 of mobile gas processing plant 120. Dehy unit 330 may further include a BTEX combustor disposed in the contact tower. The contact tower has an inlet at a bottom portion thereof and an outlet at a top portion. After the filtered gas leaves inlet filter separator 325, it may flow into dehydration unit 330 from the inlet of the contact tower. As the gas enters dehy unit 330, the gas may be super-heated as it travels up the contact tower evaporating or separating all of the moisture and other impurities and/or contaminants in the gas stream. More specifically, the BTEX combustor of dehy unit 330 may be configured to heat the filtered gas as it travels up the tower toward the outlet thereof. To heat the gas, the BTEX combustor may use triethylene glycol as fuel from TEG regen skid 332 which is also disposed on mobile gas processing plant 120. For example, the inlet gas may be heated to a temperature of around 350° in the contact tower by the BTEX combustor, and as a result, any contamination product in the hydrocarbon gas stream may be burned off in the contact tower. Also, any liquid remaining in the hydrocarbon gas in the tower may evaporate and separate from the gas stream as it passes through the contact tower. Any liquids that are in vaporous form in the hydrocarbon gas may evaporate and drop out as well, and clean hot gas would flow out from the contact tower outlet. Such an arrangement with the BTEX combustor inside the contact tower allows the system to work in populated areas as well where flaring is not possible.

At block 930, the clean hot gas stream flowing out of dehydration unit 330 flows through a second JT unit to reduce the pressure and temperature of the hot gas to operating requirements. In the embodiment shown in FIGS. 3-7, at block 930, the clean hot gas stream flowing out of dehy unit 330 flows through second JT unit 335. Like first JT unit 315, second JT unit 335 may also include at least two JT valves or porous plugs. Thus, the first JT valve of second JT unit 315 (e.g., digital or electronic JT valve) may work as a primary valve and the second JT valve of second JT unit 335 (e.g., pneumatic JT valve) may work as a backup in the event the first JT valve fails. Second JT unit 315 also produces the Joule-Thomson effect on the hydrocarbon gas passing therethrough by forcing the gas through the (first or second) JT valve or porous plug thereof while keeping the gas insulated so that no heat exchange occurs, thereby causing a temperature drop and a pressure drop (e.g., pressure cut) of the gas.

The at least two JT valves of second JT unit 335 may also be controlled by one or more of electronic, pneumatic, and hydraulic means to automatically set one of the at least two JT valves of second JT unit 335 to be in operation at a given time. Thus, during operation, if control unit 370 detects a trim or other problem on the first JT valve of second JT unit 335 that is currently in operation, control unit 370 may automatically shut the first JT valve and switch the gas flow to pass through a second JT valve of second JT unit 335, thereby ensuring continuous operation of second JT unit 335 without requiring shutdown of the whole system even in the event of a valve failure. By providing redundant JT valves having identical function for second JT unit 335, continuous operation of mobile plant 120 can be achieved even when a technician needs to repair or replace a malfunctioning JT valve. Control unit 370 may be configured to electronically control (e.g., using electronic or pneumatic actuators) the operation to shut the first JT valve and to switch the gas flow to pass through the second JT valve of second JT unit 335. Further, the at least two JT valves or porous plugs of second JT unit 335 may be set (e.g., by control unit 370) to produce a desired outlet pressure for the gas flowing out of second JT unit 335, based on system or downstream requirements. Thus, the hot gas stream flowing into second JT unit 335 will take a pressure cut to the desired outlet pressure, thus dropping the dew point again to remove any liquids that still remain in vaporized form in the hot gas stream flowing into second JT unit 335. This results in an increase in a proportion of free liquids (e.g., NGLs, water) and/or condensate in the gas by going from a vaporized or aerosol form to a liquidized form, thereby further purifying and drying the hydrocarbon gas.

Next, at block 935, the hydrocarbon gas processed at block 930 passes through a vertical separator. In the embodiment shown in FIGS. 3-7, at block 935, the hydrocarbon gas passes through vertical separator 340 (e.g., pre-filter liquid knockout unit). Vertical separator 340 is a two-phase separator vessel (e.g., 24" vertical separator) that will allow the gas portion of the hydrocarbon gas stream to pass through and catch any liquids to be separated and transported to a designated pipeline or containment for removal. The bottom of vertical separator 340 may be coupled to the drain line that is also coupled to inlet scrubber 320 and to inlet filter separator 345. Any liquids collected at the bottom of vertical separator 340 may be drained via the drain line.

Method 900 then proceeds to block 940, where the hydrocarbon gas stream processed at block 935 flows through an outlet filter separator. In the embodiment shown in FIGS. 3-7, at block 940, the hydrocarbon gas stream passes through outlet filter separator (e.g., coalescing unit) 345 for further processing (e.g., filtration, purification, cleaning) of the hydrocarbon gas. Like inlet filter separator 325, outlet filter separator 345 may also include a filter bank of one or more gas filters (or series of gas filters) set at predetermined micron levels (e.g., gas filters up to around 3-4 microns) to filter out or clean the gas of any remaining vapors or particulates (e.g., elemental sulfurs, airborne particulates, and the like) that may remain in the gas stream. As the hydrocarbon gas stream passes through the series of gas filters of the filter bank of outlet filter separator 345, the hydrocarbon gas becomes further purified by removal of liquids, airborne condensate and particulate matter, and any liquids and particulates filtered out at outlet filter separator 345 may fall to a bottom or boot of outlet filter separator 345 and may be disposed of in the same manner as the liquids removed at inlet scrubber 320. Finally, at block 945, processed (dry) hydrocarbon gas flowing out through the outlet filter separator 345 is output via an outlet from the mobile gas processing plant for use as sales quality fuel. In the embodiment shown in FIGS. 3-7, at block 945, filtered dry gas flowing out from outlet filter separator 345 is output from outlet 350 to the output line connected to mobile gas processing plant 120.

At some locations, it may be undesirable to use the contact tower of dehy unit 330 to heat and clean the hydrocarbon gas mixture during the hydrocarbon gas processing with mobile gas processing plant 120. In an alternate embodiment, as illustrated by method 1000 of FIG. 10 described in detail below, dual pass line heater 360 may be used instead of dehy unit 330 during the hydrocarbon gas processing to break and remove liquids before the processed gas is output from mobile gas processing plant 120. Dual pass line heater 360 includes first and second heating coils through which the process gas stream passes and a heater that heats the hydrocarbon gas in the heating coils through indirect heat. The first and second heating coils of dual pass line heater 360 can be configured to operate in different configurations. For example, dual pass line heater 360 may have 12 passes (e.g., 12 different turns heating the gas) through which the process gas stream passes, where 8 of the passes or turns correspond to the first heating coil, and 4 of the passes or turns correspond to the second heating coil. During operation, the 12 passes of the first and second heating coils of dual pass line heater 360 may be configured to operate as a single pass line heater with the process stream passing through all 12 passes or turns as a continuous flow path. Alternately, the first heating coil may operate as a first pass line heater and the second heating coil may operate as a second pass line heater such that the process gas stream passes through the flow path of the first heating coil, then the process gas stream passes through a flow path of one or more other components of mobile gas processing plant 120, and thereafter, the process gas stream passes through the flow path of the second heating coil. In the embodiment of method 900 of FIG. 9, first and second heating coils of dual pass line heater 360 may be bypassed altogether, and dehy unit 330 may be used to heat the hydrocarbon gas stream.

Figure 10:
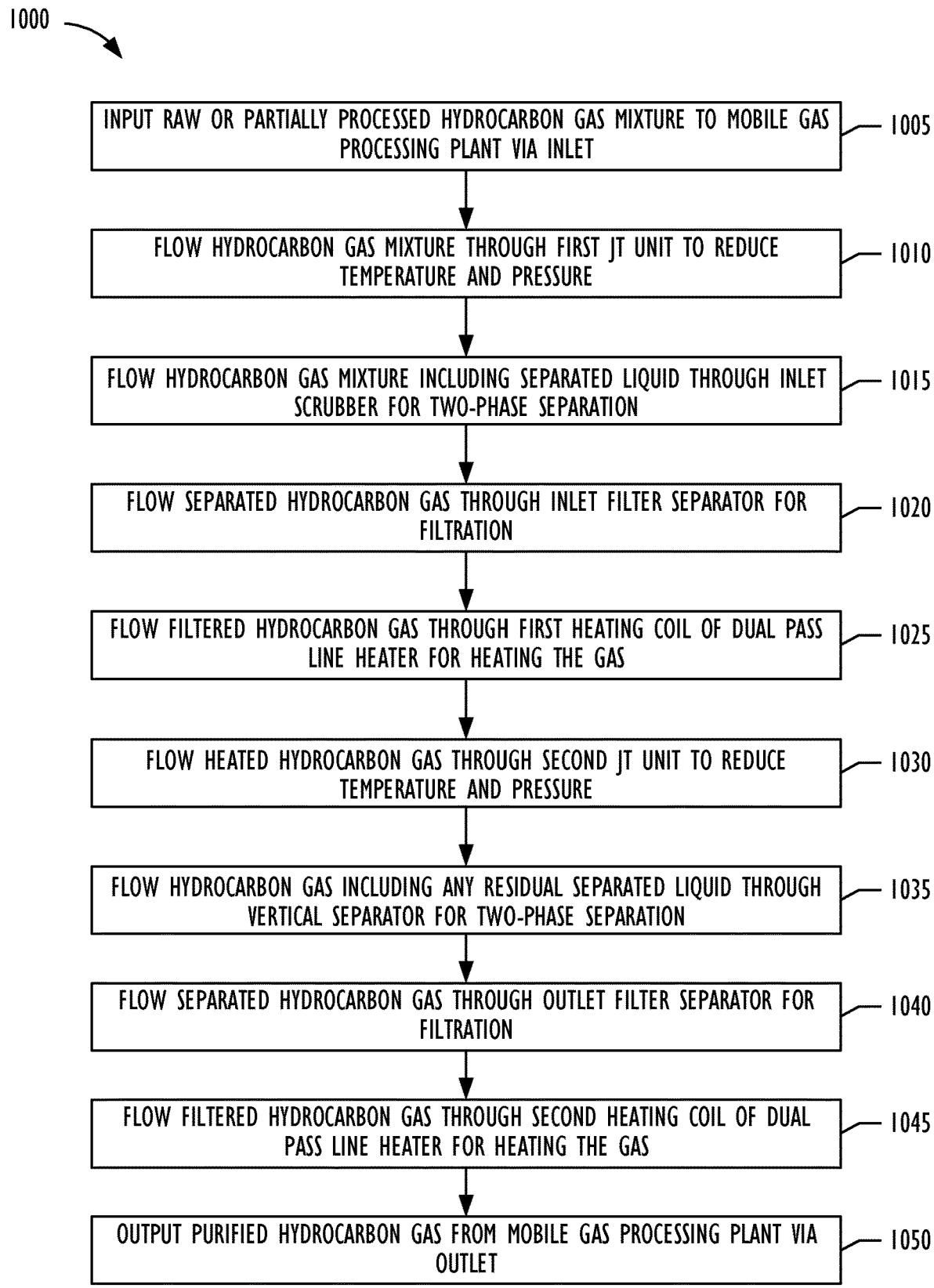
FIG. 10 is a flow chart illustrating another method for processing input hydrocarbon gas mixture with a mobile gas processing plant.

FIG. 10 is a flow chart illustrating alternate method 1000 for processing a hydrocarbon gas mixture with mobile gas processing plant 120. Like method 900, method 1000 can be performed by mobile gas processing plant 120 after the plant is in the operational mode. Although FIG. 10 illustrates that blocks of method 1000 are implemented in a particular sequential order of operations, method 1000 is not limited to this order of operations, and instead, other embodiments of method 1000 may have one or more blocks implemented in a different order, one or more blocks omitted, and/or one or more blocks replaced with other blocks.

In the embodiment shown in FIGS. 3-7, mobile gas processing plant 120 is configured to be switchable between the gas processing method as per method 900 of FIG. 9 and the gas processing method as per method 1000 of FIG. 10, by an operation of a user. Alternately, mobile gas processing plant 120 can be automatically switched between the gas processing method as per method 900 of FIG. 9, and the gas processing method as per method 1000 of FIG. 10 by implementing a programmable logic controller. Operations performed at blocks 1005-1020 of method 1000 are the same as the operations performed at blocks 905-920 of method 900 of FIG. 9, and detailed description thereof is omitted here. At block 1025, the hydrocarbon gas separated at block 1020 passes through a first pass of dual pass line heater 360. In the embodiment shown in FIGS. 3-7, at block 1025, the hydrocarbon gas filtered and separated at inlet filter separator 325 goes to the first heating coil of dual pass line heater 360 for further processing (e.g., heating, purification, cleaning). For example, in case dual pass line heater 360 has 12 passes where 8 of the passes (e.g., sections, turns) correspond to the first heating coil, and 4 of the passes (e.g., sections, turns) correspond to the second heating coil, at block 1025, the hydrocarbon gas filtered and separated at inlet filter separator 325 flows through the 8 passes of the first heating coil of dual pass line heater 360. At the first heating coil, the process gas stream may be heated as it travels through the first heating coil, thereby re-vaporizing the hydrocarbon gas mixture above the dew point and flowing out heated gas from the first heating coil of dual pass line heater 360.

Method 1000 then proceeds to block 1030 where the heated gas flowing out from the first heating coil of dual pass line heater 360 flows into second JT unit 335. Operations performed at blocks 1030-1040 of method 1000 are the same as the operations performed at blocks 930-940 of method 900 of FIG. 9, and detailed description thereof is omitted here. Thus, at blocks 1030-1040, after the process gas stream is heated by the first heating coil of dual pass line heater 360, the heated gas stream flows into second JT unit 335 (Block 1030) where the heated gas takes another pressure cut and reduction in temperature (based on desired output pressure for the gas stream), then go through vertical separator 340 (Block 1035) that will separate out from the gas stream, any liquids that were created by the gas stream passing through second JT unit 335, and then the separated gas will go through outlet filter separator 345 (Block 1040) to filter out particulates, liquids, and other contaminants and/or impurities that still remain in the gas stream.

Next, at block 1045, the hydrocarbon gas processed at block 1040 flows through the second heating coil of dual pass line heater 360. In the embodiment shown in FIGS. 3-7, at block 1045, the hydrocarbon gas filtered and separated at outlet filter separator 345 flows to the second heating coil of dual pass line heater 360 for further processing. Continuing with the above example where dual pass line heater 360 has 12 passes where 8 of the passes correspond to the first heating coil, and 4 of the passes correspond to the second heating coil, at block 1045, the hydrocarbon gas filtered and separated at outlet filter separator 345 flows through the 4 passes of the second heating coil. At the second heating coil, the gas may be heated again as it travels therethrough, thereby heating the gas again above the dew point, and vaporizing off or evaporating out any liquids that still remain in the gas stream before the gas is output via outlet 350. At block 1050, processed (dry) hydrocarbon gas flowing out through the second heating coil of dual pass line heater is output from mobile gas processing plant. In the embodiment shown in FIGS. 3-7, at block 1050, filtered dry gas (e.g., pure strength gas, sales quality gas, dry natural gas) flowing out from the second heating coil of dual pass line heater 360 is output from outlet 350 of mobile gas processing plant 120 to an output line coupled to outlet 350.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means ±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise.

What is claimed is:

1. A mobile gas processing transport, comprising:
a base frame;
an inlet and an outlet;
a first Joule-Thompson (JT) valve unit, and a second JT valve unit, wherein each of the first and second JT valve units includes a first JT valve and a second JT valve, and wherein in an operational mode, and for each of the first and second JT valve units, a hydrocarbon gas stream flows through one of the first and second JT valves operating as a primary valve and does not flow through the other of the first and second JT valves operating as a backup valve;
an actuator for the first JT valve unit;
a control unit that is configured to control the actuator to shut the first JT valve of the first JT valve unit and switch the hydrocarbon gas stream to flow through the second valve of the first JT valve unit in response to detecting a failure condition;
an inlet scrubber;
a dehydration unit including a contact tower;
an inlet filter separator and an outlet filter separator; and
a vertical separator;
wherein the first and second JT valve units, the actuator, the inlet scrubber, the dehydration unit, the inlet and outlet filter separators, and the vertical separator, are mounted on the base frame of the mobile gas processing transport.

2. The mobile gas processing transport according to claim 1, wherein the mobile gas processing transport is configured to input a hydrocarbon gas mixture from the inlet, process the hydrocarbon gas mixture to separate dry hydrocarbon gas from a residual mixture in the hydrocarbon gas mixture, and output, from the outlet, the dry hydrocarbon gas to be used as fuel by a gas turbine of a mobile electric power generation transport.

3. The mobile gas processing transport according to claim 2, wherein the input hydrocarbon gas mixture is a raw hydrocarbon gas mixture output from a producing wellhead, or a partially processed hydrocarbon gas mixture output from an amine unit.

4. The mobile gas processing transport according to claim 2, wherein the residual mixture separated from the hydrocarbon gas mixture includes one or more of: higher molecular mass hydrocarbons, impurities, and contaminants.

5. The mobile gas processing transport according to claim 2, wherein the residual mixture separated from the hydrocarbon gas mixture includes one or more of natural gas liquids, crude oil, carbon dioxide, carbon monoxide, hydrogen sulfide, mercaptans, nitrogen, helium, liquid water, water vapor, sand, mercury, and airborne particulates.

6. The mobile gas processing transport according to claim 2, wherein the dry hydrocarbon gas separated from the hydrocarbon gas mixture is a pure strength, sales quality natural gas that is suitable for use as fuel by a gas turbine.

7. The mobile gas processing transport according to claim 2, wherein an energy rating of the input hydrocarbon gas mixture is in a range of 1300-1350 BTUs, and an energy rating of the output dry hydrocarbon gas is in a range of 1000-1100 BTUs.

8. The mobile gas processing transport according to claim 2, wherein each of the inlet filter separator and the outlet filter separator includes a filter bank that has at least one air filter for removing airborne particulates from the input hydrocarbon gas mixture, and wherein a micron rating of the at least one air filter is in a range of 3-4 microns.

9. The mobile gas processing transport according to claim 2, wherein the dehydration unit includes a contact tower and a btex combustor disposed in the contact tower for heating the input hydrocarbon gas mixture flowing through the contact tower, and
  wherein the contact tower is mounted to the base frame such that the contact tower is rotated up to be in an upright position relative to the base frame in an operational mode, and the contact tower is rotated down to be in a prostrated position relative to the base frame in a transportation mode.

10. The mobile gas processing transport according to claim 9, wherein the contact tower is rotatable between the upright position and the prostrated position using hydraulics, pneumatics, or an electric motor, without using mechanical apparatus external to the mobile gas processing transport.

11. The mobile gas processing transport according to claim 9, wherein a base of the contact tower is mounted to the base frame with a hinge to enable the contact tower to be rotatable relative to the base frame between the upright position and the prostrated position.

12. The mobile gas processing transport according to claim 1, wherein the actuator is a first actuator and the mobile gas processing transport further comprises a second actuator for the second JT valve unit,
  wherein the control unit is further configured to, during the operational mode and for the second JT valve unit;
  detect a failure condition for the primary valve; and
  switch the hydrocarbon gas stream to flow through the backup valve in response to detecting the failure condition.

13. The mobile gas processing transport according to claim 1, wherein the primary valve is a digital or electronic JT valve, and the backup valve is a pneumatic JT valve.

14. The mobile gas processing transport according to claim 2, wherein each of the inlet scrubber and the vertical separator is a two-phase separator that is configured to separate a liquid-phase from a gas-phase in the hydrocarbon gas mixture.

15. The mobile gas processing transport according to claim 1, further comprising a dual pass line heater that includes a first heating coil and a second heating coil.

16. A mobile gas processing plant, comprising:
  an inlet and an outlet;
  first and second Joule-Thompson (JT) valve units;
  an inlet scrubber;
  a dehydration unit including a contact tower;
  inlet and outlet filter separators;
  a vertical separator; and
  a dual pass line heater including first and second heating coils;
  wherein the mobile gas processing plant is a mobile unit that is permanently mounted on a base frame of a transport; and
  wherein the dehydration unit includes a contact tower, and
    wherein the contact tower is permanently mounted on the base frame of the transport such that the contact tower is rotated up to be in an upright position relative to the base frame of the transport in an operational mode, and the contact tower is rotated down to be in a prostrated position relative to the base frame in a transportation mode.

17. The mobile gas processing plant according to claim 16, wherein the contact tower is rotatable between the upright position and the prostrated position using hydraulics, pneumatics, or an electric motor, and without using mechanical apparatus external to the at least one transport.

18. The mobile gas processing plant according to claim 16, wherein each of the first and second JT valve units includes a first JT valve and a second JT valve, and wherein in the operational mode, and for each of the first and second JT valve units, a hydrocarbon gas stream flows through one of the first and second JT valves operating as a primary valve, and does not flow through the other of the first and second JT valves operating as a backup valve.

19. The mobile gas processing plant according to claim 18, further comprising a control unit that is configured to, during the operational mode and for each of the first and second JT valve units:
  detect a failure condition for the primary valve; and
  switch the hydrocarbon gas stream to flow through the backup valve in response to detecting the failure condition.

* * * * *